United States Patent [19]

Betts et al.

[11] Patent Number: 5,554,606

[45] Date of Patent: *Sep. 10, 1996

[54] ANTIBIOTIC COMPOUNDS

[75] Inventors: Michael J. Betts, Wilmslow; Gloria A. Breault, Congleton, both of England

[73] Assignee: Zeneca Limited, London, United Kingdom

[ * ] Notice: The term of this patent shall not extend beyond the expiration date of Pat. No. 5,478,820.

[21] Appl. No.: 329,614

[22] Filed: Oct. 26, 1994

Related U.S. Application Data

[63] Continuation of Ser. No. 129,149, filed as PCT/GB92/00586, published as WO92/18582, Oct. 29, 1992, abandoned.

[30] Foreign Application Priority Data

Mar. 12, 1990 [GB] United Kingdom ............... 9005469
Apr. 8, 1991 [GB] United Kingdom ............... 9107363

[51] Int. Cl.$^6$ .................... C07D 487/04; A61K 31/40
[52] U.S. Cl. .................................. 514/210; 540/350
[58] Field of Search ........................... 514/210; 540/350

[56] References Cited

U.S. PATENT DOCUMENTS

| | | | |
|---|---|---|---|
| 4,933,333 | 6/1990 | Sunagawa et al. | 514/192 |
| 4,943,569 | 7/1990 | Sunagawa | 514/210 |
| 4,962,103 | 10/1990 | Sunagawa | 514/210 |
| 4,963,544 | 10/1990 | Murata et al. | 514/210 |
| 5,093,328 | 3/1992 | Sunagawa et al. | 514/210 |
| 5,102,997 | 4/1992 | Sugimura et al. | 540/350 |
| 5,194,624 | 3/1993 | Murata et al. | 514/210 |
| 5,215,983 | 6/1993 | Murata et al. | 514/210 |

FOREIGN PATENT DOCUMENTS

| | | |
|---|---|---|
| 0126587 | 11/1984 | European Pat. Off. . |
| 0182213 | 5/1986 | European Pat. Off. . |
| 0243686 | 11/1987 | European Pat. Off. . |
| 0443883 | 8/1991 | European Pat. Off. . |
| 0472062 | 2/1992 | European Pat. Off. . |

*Primary Examiner*—Rebecca Cook
*Attorney, Agent, or Firm*—Cushman Darby & Cushman, L.L.P.

[57] ABSTRACT

The present invention provides a compound of the formula (I)

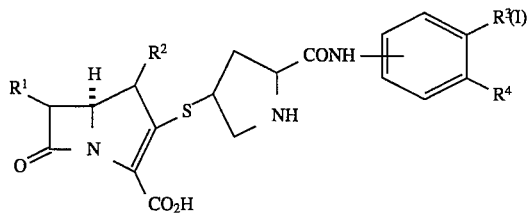

wherein:

$R^1$ is 1-hydroxyethyl, 1-fluoroethyl or hydroxymethyl;

$R^2$ is hydrogen or $C_{1-4}$ alkyl;

$R^3$ and $R^4$ are ortho with respect to one another wherein $R^3$ and $R^4$ are independently hydroxy or in vivo hydrolyzable esters thereof; the benzene ring being optionally further substituted; or a pharmaceutically acceptable salt or in vivo hydrolyzable ester thereof.

15 Claims, No Drawings

ANTIBIOTIC COMPOUNDS

This is a continuation of application Ser. No. 08/129,149, filed on Oct. 6, 1993, which was abandoned upon the filing hereof a 371 of PCT/GB 92/00586 filed Apr. 2, 1992, published as WO92/18582 on Oct. 29, 1992.

The present invention relates to carbapenems and in particular to such compounds containing a dihydroxybenzene or related group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with particularly good antibacterial activity in particular against strains of *Pseudomonas aeruginosa* and those strains of this organism which have been shown to be resistant to imipenem. They exhibit good stability to beta-lactamases. In addition many of the compounds of this invention exhibit favourable pharmacokinetics.

The carbapenem derivatives referred to herein are named in accordance with the generally accepted semi-systematic nomenclature:

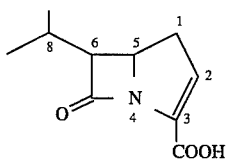

Accordingly the present invention provides a compound of the formula (I)

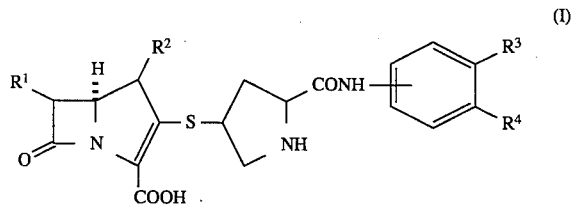

(I)

wherein:
$R^1$ is 1-hydroxyethyl, 1-fluoroethyl or hydroxymethyl;
$R^2$ is hydrogen or $C_{1-4}$ alkyl;
$R^3$ and $R^4$ are ortho with respect to one another wherein $R^3$ and $R^4$ are independently hydroxy or in vivo hydrolysable esters thereof; the benzene ring being optionally further substituted; or a pharmaceutically acceptable salt or in vivo hydrolysable precursor thereof.

Preferably $R^1$ is 1-hydroxyethyl.

$R^2$ is hydrogen or $C_{1-4}$alkyl for example methyl, ethyl, n-propyl, isopropyl and n-butyl. Preferably $R^2$ is hydrogen or methyl and in particular $R^2$ is methyl.

$R^3$ is hydroxy or an in vivo hydrolysable ester thereof. $R^4$ is hydroxy or an in vivo hydrolysable ester thereof.

In vivo hydrolysable esters are those pharmacetuically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-ethoxycarbonyloxyethyl and may be formed at any carboxy group in the compound of this invention.

Conveniently $R^3$ and $R^4$ have the same value and are both hydroxy or are both in vivo hydrolysable esters, for example they are both acetoxy or pivaloyloxy.

As stated hereinbefore the benzene ring is optionally further substituted. Particular optional substituents include $C_{1-4}$alkyl for example methyl, ethyl or isopropyl; halo for example chloro, bromo or fluoro; hydroxy; hydroxy$C_{1-4}$alkyl for example hydroxymethyl or hydroxyethyl; amino; nitro; $C_{1-4}$alkoxy for example methoxy or ethoxy; carboxy$C_{1-4}$alkyl for example carboxymethyl or carboxyethyl; $C_{1-4}$alkanoylamino for example acetamido; N-alkyl-N-$C_{1-4}$alkanoylamino; trifluoromethyl; carboxy; carbamoyl; $C_{1-4}$alkylcarbamoyl for example methylcarbamoyl; di-$C_{1-4}$alkylcarbamoyl for example di-[N-ethyl]carbamoyl; cyano; $C_{1-4}$alkanesulphonamido for example methanesulphonamido; $C_{1-4}$alkanoyl for example acetyl; $C_{1-4}$alkanoyloxy for example acetoxy or propionoxy; $C_{1-4}$alkoxycarbonyl for example methoxycarbonyl; $C_{1-4}$alkylthio for example methylthio, $C_{1-4}$alkanesulphinyl for example methanesulphinyl; $C_{1-4}$alkanesulphonyl for example methanesulphonyl; $C_{2-4}$alkenyl for example allyl or vinyl; hydroxyiminomethyl (HON=CH—); $C_{1-4}$alkoxyiminomethyl for example methoxyiminomethyl; aminosulphonyl; N-$C_{1-4}$alkylaminosulphonyl for example N-methylaminosulphonyl; and di-[N-$C_{1-4}$alkyl]aminosulphonyl for example di-[N-methyl]aminosulphonyl.

Favoured optional substituents for the benzene ring are fluoro, bromo, chloro, cyano, nitro, carboxymethyl, hydroxy, di-[N-methyl]carbamoyl, methanesulphonyl, di-[N-ethyl]aminosulphonyl and methoxycarbonyl.

The skilled man will realise that the benzene ring may have up to 3 optional substituents, which may be the same or different, are possible. In general we prefer up to 2 optional substituents.

The present invention covers all epimeric, diastereoisomeric and tautomeric forms of the compounds of the formula (I) except where otherwise indicated. The compounds of the formula (I) have a number of centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

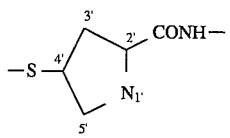

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

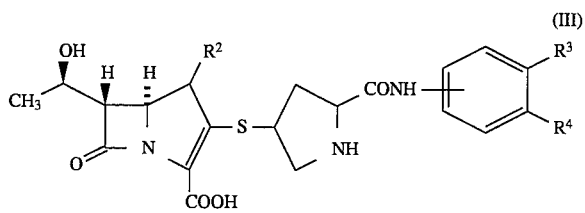

and pharmaceutically acceptable salts and in vivo hydrolysable esters thereof, wherein $R^2$, $R^3$ and $R^4$ are as hereinbefore defined and the benzene ring is further optionally substituted.

In the formulae herein, when a bond is represented as a wedge, this idicates that in three dimensions the bond would be coming forward out of the paper and when a bond is represented as hatched this bond would be going back into the paper.

When $R^2$ is $C_{1-4}$alkyl for example methyl it is preferred that the compound is in the form of the 1R configuration.

A particularly preferred class of compounds of the present invention is that of the formula (IV):

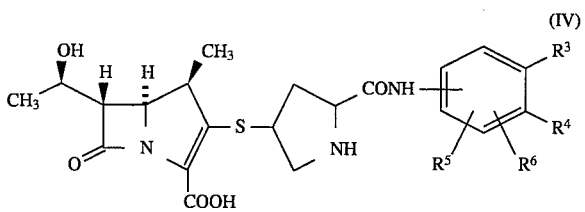

wherein $R^3$ and $R^4$ are hereinbefore defined and $R^5$ and $R^6$ are independently hydrogen, halo, cyano, nitro, carboxy, carboxymethyl, methanesulphonyl, di-[N-methyl]carbamoyl, di-[N-ethyl]aminosulphonyl and hydroxy. Preferably the benzene ring is substituted by $R^3$ and $R^4$ in positions 3 and 4 relative to the amido linking group. Particular substitution patterns for the benzene ring include: 3,4-dihydroxybenzene, 3,4-dihydroxy-5-bromo-benzene, 2,5-dichloro-3, 4-dihydroxybenzene, 3,4,5-trihydroxybenzene, 3,4-dihydroxy-6-methoxycarbonylbenzene, 3,4-dihydroxy-5-cyanobenzene and 3,4-dihydroxy-6-di-[N-ethyl] aminosulphonylbenzene.

Particular compounds of the present invention are
(5R,6S,8R,2'S,4'S)-2-(2-(3,4-dihydroxyphenylcarbamoyl)pyrrolidin- 4-ylthio)-6-(1-hydroxyethyl)carbapenem-3-carboxylic acid;
(1R,5R,6S,8R,2'S,4'S)-2-(2-(5-cyano- 3,4-dihydroxyphenylcarbamoyl)-pyrrolidin-4-ylthio)-6-(1-hydroxyethyl)-1-methylcarbapenem-3-carboxylic acid;
(5R,6S,8R,2'S,4'S)-2-(2-(5-bromo-3,4-dihydroxyphenylcarbamoyl)-pyrrolidin- 4-ylthio)-6-(1-hydroxyethyl)carbapenem-3-carboxylic acid;
(1R,5R,6S,8R,2'S,4'S)-2-(2-(3,4-dihydroxyphenylcarbamoyl)-pyrrolidin- 4-ylthio)-6-(1-hydroxyethyl)-1-methylcarbapenem-3-carboxylic acid;
(1R,5R,6S,8R,2'S,4'S)-2-(2-(5-methoxy- 3,4-dihydroxyphenylcarbamoyl)-pyrrolidin-4-ylthio)-6-(1-hydroxyethyl)-1-methylcarbapenem-3-carboxylic acid;
(1R,5R,6S,8R,2'S,4'S)-2-(2-(2,5-dichloro- 3,4-dihydroxyphenyl-carbamoyl)pyrrolidin-4-ylthio)-6-(1-hydroxyethyl)-1-methylcarbapenem- 3-carboxylic acid;
(1R,5R,6S,8R,2'S,4'S)-2-(2-(5-hydroxy- 3,4-dihydroxyphenylcarbamoyl)-pyrrolidin-4-ylthio)-6-(1-hydroxyethyl)-1-methylcarbapenem-3-carboxylic acid;
(1R,5R,6S,8R,2'S,4'S)-2-(2-(5-bromo- 3,4-dihydroxyphenylcarbamoyl)-pyrrolidin-4-ylthio)-6-(1-hydroxyethyl)-1-methylcarbapenem-3-carboxylic acid;
(1R,5R,6S,8R,2'S,4'S)-2-(2-(5-N-methoxyiminomethyl- 3,4-dihydroxy-phenylcarbamoyl)pyrrolidin-4-ylthio)-6-(1-hydroxyethyl)- 1-methyl-carbapenem-3-carboxylic acid;
(1R,5R,6S,8R,2'S,4'S)-2-(2-(6-methoxycarbonyl- 3,4-dihydroxyphenyl-carbamoyl)pyrrolidin-4-ylthio)-6-(1-hydroxyethyl)-1-methylcarbapenem- 3-carboxylic acid;
(1R,5R,6S,8R,2'S,4'S)-2-(2-(6-carboxy- 3,4-dihydroxyphenylcarbamoyl)-pyrrolidin-4-ylthio)-6-(1-hydroxyethyl)-1-methylcarbapenem-3-carboxylic acid; and
(1R,5R,6S,8R,2'S,4'S)-2-(2-(6-di-(N-ethyl)aminosulphonyl- 3,4-dihydroxyphenylcarbamoyl)pyrrolidin-4-ylthio)-6-(1-hydroxyethyl)- 1-methylcarbapenem-3-carboxylic acid;

Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine, or amino acids, for example, lysine.

For the avoidance of doubt there may be two or three salt forming counter ions depending on the number and type of charged functions and the valency of the counter ions.

In order to use a compound of the present invention or a pharmaceutically acceptable salt or in vivo hydrolysable precursor thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable precursor thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid), inhibitors of metabolising enzymes (for example inhibitors of peptidases, for example Z-2-acylamino-3-substituted propenoates such as cilastatin) and N-acylated amino acids (for example see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

The pharmaceutical compositions of the invention will normally be administered to man in order to combat infections caused by bacteria, in the same general manner as that employed for imipenem due allowance being made in terms of dose levels for the potency of the compound of the present invention relative to the clinical use of imipenem. Thus each patient will receive a daily intravenous, subcutaneous or intramuscular dose of 0.05 to 5 g., and preferably 0.1 to 2.5 g., of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.5 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V):

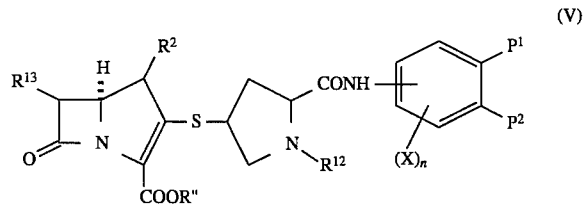

(V)

wherein $R^2$ is as hereinbefore defined; $R^{13}$ is a group $R^1$ or 1-(protected hydroxy)ethyl; $R^{11}$ is hydrogen or a carboxy protecting group; $R^{12}$ is hydrogen or an amino protecting group, and are $P^1$ $P^2$ independently hydroxy or protected hydroxy and $(X)_n$ represents up to three optional substituents which may be the same or different; with the proviso that there is at least one protecting group: and thereafter if necessary:

(i) forming a pharmaceutically acceptable salt,
(ii) esterifying to form an in vivo hydrolysable ester.

The compounds of the formula (V) are novel and form another aspect of the invention.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); diaryl(lower alkyl)silyl groups (eg t-butyldiphenylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups. In addition two hydroxy groups substituted on adjacent carbon atoms, for example in the catechol moiety, may be protected in the form of a cyclic silyl ether.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups; and the phthalimido group.

Methods appropriate for removal of hydroxy and amino protecting groups include, for example, acid-. base-, metal-, or enzymically-catalysed hydrolysis, for groups such as p-nitrogenzyloxycarbonyl, hydrogenation and for groups such as o-nitrobenzyloxycarbonyl, photolyrically.

In another aspect of the present invention the compounds of the formula (I) or pharmaceutically acceptable salts or in vivo hydrolysable esters thereof and compounds of the formula (V) may be prepared by:

a) reacting compounds of the formulae (VI) and (VII):

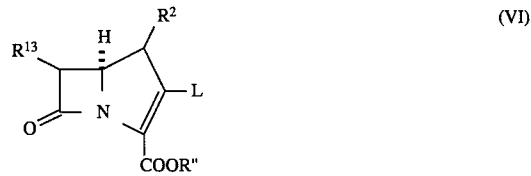

(VI)

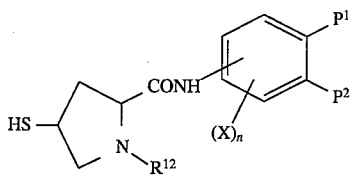

wherein $P^1$, $P^2$, $R^2$, X, n, $R^{11}$, $R^{12}$ and $R^{13}$ are as hereinbefore defined and L is a leaving group, or b) cyclising a compound of the formula (VIII):

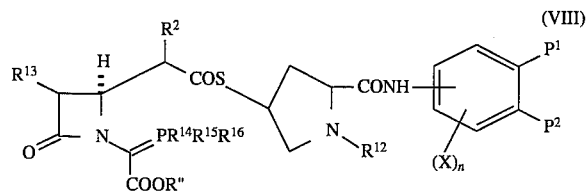

wherein $P^1$, $P^2$, X, n, $R^2$, $R^{11}$, $R^{12}$ and $R^{13}$ and are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy; wherein any functional group is optionally protected and thereinafter if necessary:

(i) removing any protecting groups;
(ii) forming a pharmaceutically acceptable salt;
(iii) esterifying to form an in vivo hydrolysable ester.

Suitably L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SO—CH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between –25° C. and ambient, suitably at about 0° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

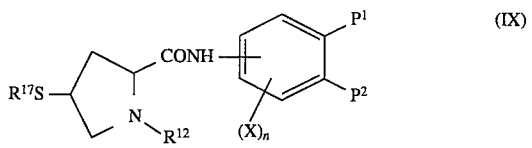

wherein $P^1$, $P^2$, X, n and $R^{12}$ are as hereinbefore defined and $R^{17}$ is a protecting group, for example $C_{1-6}$alkanoyl or $C_{1-6}$ alkoxycarbonyl. Preferred values for $R^{17}$ are acetyl and S-butoxycarbonyl. The compounds of the formula (IX) can be converted to the compounds of the formula (VII) by standard methods of deprotection, for example acetyl groups can be removed by basic hydrolysis in aqueous alkanol, alkenol for example allyl alcohol or tetrahydrofuran.

The compounds of the formula (IX) are novel and form another aspect of the present invention.

The compounds of the formula (IX) may be prepared by the reaction of a compound of the formula (X) or activated derivative thereof which may be formed in situ with a compound of the formula (XI):

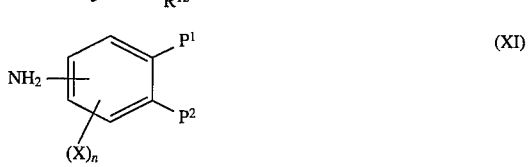

wherein $P^1$, $P^2$, X, n, and are as hereinbefore defined. Activated derivatives of the compound of the formula (X) include activated esters, anhydrides such as 1H-benzo[1,2,3]triazol-1-yl, pentafluorophenyl and 2,4,5-trichlorophenyl esters or the benzimidazol-2-yl ester of the thiocarboxylic acid corresponding to (X) and acid halides. The reaction of the compounds of the formulae (X) and (XI) is performed under standard methods of acylating anilines and related compounds, for example in the presence of Vilsmeier reagent (thus forming the reactive derivative of (X) in situ) at temperatures in the range of –30° C. to +25° C., preferably in the region –20° C. to +5° C., or in the presence of sulphonyl chloride at ambient temperature.

The compounds of the formulae (X) and (XI) are prepared by standard methods known to the skilled man such as the methods of the Examples hereinafter, or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally substituted phenoxy; di-$C_{1-6}$alkylamino such as dimethylamino or diethylamino; diarylamino such as diphenylamino or any two of $R^{14}$–$R^{16}$ represent o-phenylenedioxy. Preferably each of $R^{14}$–$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

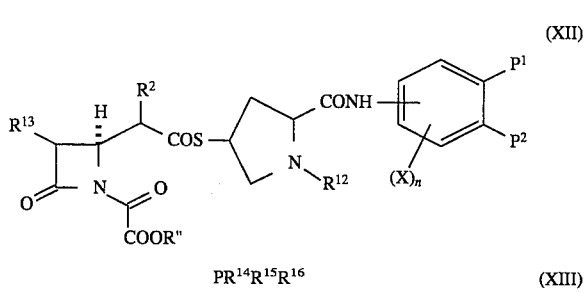

(XII)

$PR^{14}R^{15}R^{16}$ (XIII)

wherein $R^2$, X, n, $R^{11}$–$R^{16}$, $P^1$ and $P^2$ are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

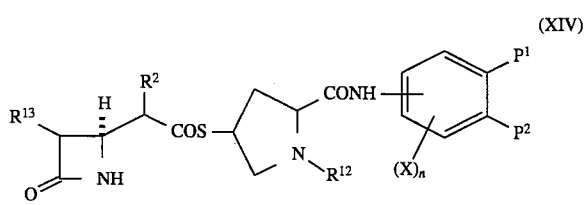

(XIV)

wherein $R^2$, $R^{12}$, $R^{13}$, X, n, $P^1$ and $P^2$ are as hereinbefore defined with a compound of the formula (XV):

Cl—CO—COOR$^{11}$ (XV)

wherein $R^{11}$ is as hereinbefore defined.

The compounds of the formula (XIV) may be prepared by reacting compounds of the formulae (XVI) and (VII):

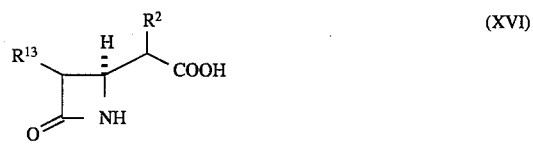

(XVI)

wherein $R^2$, X, n, $R^{12}$, $R^{13}$, $P^1$ and $P^2$ are as hereinbefore defined. The compounds of the formula (XVI) are known in the art and may be reacted with compounds of the formula (VII) under conventional acylation conditions known in the art.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have particularly high activity in vitro against strains of Pseudomonas aeruginosa and other Gram-negative aerobic bacteria.

The antibacterial properties of the compounds of the invention may also be demonstrated in vivo in conventional tests.

Carbapenem compounds generally have been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test agar medium. The antibacterial activity is described in terms of the minimum inhibitory concentration (MIC) determined by the agar-dilution technique with an inoculum size of $10^4$ CFU/spot.

| ORGANISM | MIC (µg/ml) EXAMPLE 2 |
|---|---|
| P. aeruginosa PU21 (101028) | 0.25 |
| Ent. cloacae P99⁻ (401054) | 0.015 |
| Serr. marcesens (421003) | 0.125 |
| Pr. morganii (433001) | 0.125 |
| E. coli DCO (341098) | 0.015 |
| St. aureus 147N (601052) | 0.25 |
| S. dublin (369001) | 0.008 |
| Strep. pyogenes (681018) | 0.008 |
| P. aeruginosa 18S (101024) | 0.06 |
| P. aeruginosa 18S IMIR(101148) | 0.06 |
| B. fragilis AMP R (542008) | 0.25 |

EXAMPLE 1

(5R,6S,8R,2'S,4'S)-2-(2-(3,4-Dihydroxyphenylcarbamoyl)pyrrolidin-4-yl-thio)- 6-(1-hydroxyethyl)carbapenem-3-carboxylic acid.

A solution of p-nitrobenzyl (5R,6S,8R,2'S,4'S)- 2-(1-allyloxycarbonyl-2-(3,4-diallyloxyphenylcarbamoyl)pyrrolidin- 4-yl-thio)-6-(1-hydroxyethyl)carbapenem-3-carboxylate (0.5 mM) and dimedone (1.5 mM) in THF (14 ml) was purged with argon. A solution of tetrakis(triphenylphosphine)palladium (0.05 mM) in THF was added and the mixture was stirred under argon for 1 hour.

4-Morpholinopropane-3-sulphonic acid buffer (15 ml) was added, followed by 10% palladium on carbon (350 mg) and the mixture was hydrogenated at atmospheric pressure for 1 hour. The mixture was filtered, THF removed by evaporation, and the filtrate was washed with ethyl acetate prior to medium pressure chromatography on HP20SS resin (gradient elution with aqueous acetonitrile). The desired fractions were collected, evaporated to remove acetonitrile and freeze dried to give the title compound (12%): NMR 1.11(d, 3H); 1.83(partially obscured); 2.71(m, 1H); 2.98(q, 1H); 3.20(d, 2H); 3.23(q, 1H); 3.53(q, 1H); 3.78(m, 1H); 3.92(m, 1H); 4.04(t, 1H); 4.10(d of t, 1H); 6.63(d, 1H); 6.75(d, 1H); 7.18(s, 1H).

EXAMPLE 2

(1R,5S,6S,8R,2'S,4'S)-2-(2-(5-Cyano- 3,4-dihydroxyphenylcarbamoyl)-pyrrolidin-4-ylthio)-6-(1-hydroxyethyl)-1- methyl-carbapenem-3-carboxylic acid.

To a solution of allyl (1R,5S,6S,8R,2'S,4'S)-2-( 1-allyloxy-carbonyl-2-(3,4-diallyloxy-5-cyanophenylcarbamoyl))pyrrolidin- 4-yl-thio)-6-(1-hydroxyethyl)-1-methyl-carbapenem-3-carboxylate (0.25 mM) and Meldrum's acid (2.0 mM) in DMF (1.3 ml), under an argon atmosphere, was added a solution of tetrakis(triphenylphosphine)palladium (0.025 mM) in THF (0.2 ml). The solution was stirred, under argon with protection from the light, for 25 minutes. THF (10 ml) was added slowly to precipitate the product. The resultant suspension was stirred for 10 minutes, the product was collected by filtration, washed with tetrahydrofuran and ether and dried to give the title product (66%): NMR 1.11(2d, 6H); 1.91(m, 1H); 2.88(m, 1H); 3.20(m, 2H); 3.35(m, 1H); 3.75(m, 1H); 3.96(m, 2H); 4.19(d of d, 1H); 4.32(t, 1H); 7.23(d, 1H); 7.32(d, 1H): m/s+ve FAB(M+H)$^+$ =489.

EXAMPLES 3–12

By the general method of Example 2, the following reactions were performed:

In Example 12 dilution of the reaction with THF(10 mL) failed to give a precipitate. Therefore the product was purified as follows: The solvent was evaporated. Ether was added to the residue to give a precipitate which was triturated with ether and THF. The impure solid was dissolved in 3.5 ml of water and 1.5 ml of acetonitrile. This solution was extracted with ethyl acetate. The aqueous layer was freeze dried to give the product as a white solid.

NMR and MS Data for Examples 3–12 (Table 1)

TABLE 1

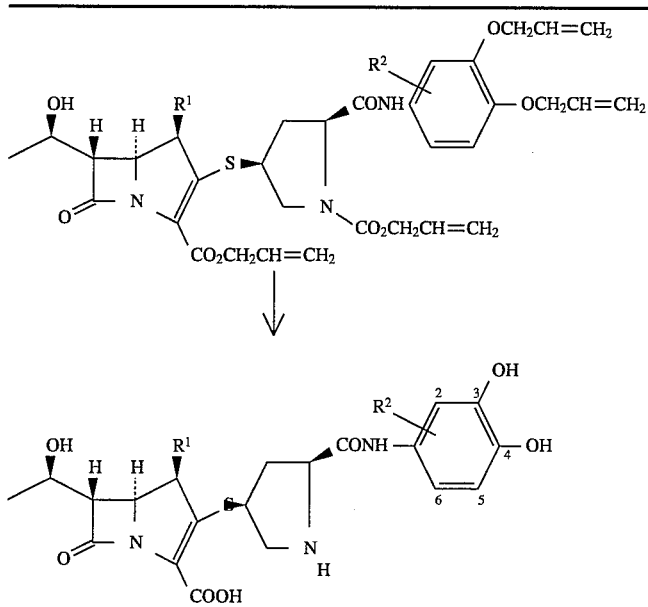

| | | | Reaction Conditions | | |
|---|---|---|---|---|---|
| Example | R$^1$ | R$^2$ | Solvent | Ratio Carbapenem: Meldrums Acid | Time (mins) |
| 3 | H | 5-Br | THF (6 ml) | 0.45 mM:1.8 mM | 60 |
| 4 | CH$_3$ | H | DMF (1.5 ml) | 0.25 mM:2.0 mM | 120 |
| 5 | CH$_3$ | 5-OCH$_3$ | DMF (1.5 ml) | 0.25 mM:2.0 mM | 25 |
| 6 | CH$_3$ | 2,5-di-Cl | THF (3 ml) | 0.2 mM:1.6 mM | 10 |
| 7 | CH$_3$ | 5-OH | DMF (0.5 ml) | 0.28 mM:2.8 mM | 45 |
| | | (from the corresponding 5-OCH$_2$CH=CH$_2$ compound) | | | |
| 8 | CH$_3$ | 5-Br | DMF (0.5 ml) | 0.27 mM:2.7 mM | 60 |
| 9 | CH$_3$ | 5-CH=NOCH$_3$ | DMF (0.25 ml) | 0.12 mM:1.2 mM | 50 |
| 10 | CH$_3$ | 6-COOCH$_3$ | DMF (0.28 ml) | 0.28 mM:2.7 mM | 105 |
| 11 | CH$_3$ | 6-COOH | DMF (0.3 ml) | 0.21 mM:2.13 mM | 75 |
| | | (from the corresponding 6-COOCH$_2$CH=CH$_2$ compound) | | | |
| 12 | CH$_3$ | 6-SO$_2$N(CH$_2$CH$_3$)$_2$ | THF/DMF (.1 ml/.2 ml) | 0.23 Mm:2.43 Mm | 160 |

FOOTNOTES:
In Examples 3 and 6 the product precipitated spontaneously from the reaction mixture. The amount of palladium-phosphine catalyst was between 0.1–0.2 equivalents compared to the carbapenem.

EXAMPLE 3: NMR: 1.11(d, 3H); 1.88(m, 1H); 2.79(m, 1H); 3.12(m, 1H); 3.21(m, 2H); 3.25(m, 1H); 3.65(m, 1H); 3.87(m, 1H); 3.93(m, 1H); 4.12(m, 1H); 4.20(m, 1H); 7.11(d, 1H); 7.21(d, 1H).

EXAMPLE 4: NMR: 1.10(2d, 6H); 1.79(m, 1H); 2.78(m, 1H); 3.03(d of d, 1H); 3.20(d of d, 1H); 3.37(m, 1H); 3.61(m, 1H); 3.82(m, 1H); 3.95(m, 1H); 4.15(m, 2H); 6.65(d, 1H); 6.80(d of d, 1H); 7.15(d, 1H): M/S+ve FAB(M+H)$^+$=464.

EXAMPLE 5: NMR: 1.11(2d, 6H); 1.89(m, 1H); 2.85(m, 1H); 3.20(m, 2H); 3.35(m, 1H); 3.71(s, 3H); 3.74(m, 1H); 3.94(m, 2H); 4.18(d of d, 1H); 4.30(d of d, 1H); 6.72(d, 1H); 6.78(d, 1H): M/S+ve FAB(M+H)+=494.

EXAMPLE 6: NMR: 1.12(2d, 6H); 1.9(partially obscured); 2.8(m, 1H); 2.98(m, 1H); 3.2(m, 1H); 3.38(m, 1H); 3.63(m, 1H); 3.8(m, 1H); 3.95(m, 1H); 4.18(d of d, 1H); 4.25(t, 1H); 7.25(s, 1H).

EXAMPLE 7: NMR: 1.12(2d, 6H); 1.78(partially obscured); 2.75(m, 1H); 2.99(m, 1H); 3.20(dd, 1H); 3.37(m, 1H); 3.55(partially obscured); 3.8(m, 1H); 3.95(quintet, 1H); 4.08(t, 1H), 4.17(dd, 1H); 6.60(s, 2H).

EXAMPLE 8: NMR: 1.12(2d, 6H); 1.70(m, 1H); 2.65(m, 1H); 2.85(m, 1H); 3.20(m, 1H); 3.45(m, 1H); 3.60(m, 1H); 3.70(m, 1H); 3.95(m, 2H); 4.15(m, 1H); 7.15(s, 1H); 7.24(s, 1H).

EXAMPLE 9: NMR: 1.15(2d, 6H); 1.79(m, 1H); 2.75(m, 1H); 2.99(m, 1H); 3.20(dd, 1H), 3.39(m, 1H); 3.59(m, 1H); 3.80(m, 1H); 3.88(s, 3H); 3.95(quintet, 1H); 4.09(t, 1H); 4.19(dd, 1H); 7.22(s, 1H); 7.29(s, 1H); 8.32(s, 1H): M/S+ve FAB(M+H)$^+$=521.

EXAMPLE 10: NMR: 1.12(d, 6H); 1.64(m, 1H); 2.62(m, 1H); 3.19(dd, 1H); 3.30–3.48(partially obscured); 3.5(m, 1H); 3.79(s, 3H); 3.89(m, 1H); 3.95(m, 1H); 4.14(m, 1H); 7.35(s, 1H); 8.2(s, 1H): M/S+ve FAB(M+H)$^+$=522.

EXAMPLE 11: NMR: 1.12(d, 6H); 1.68(m, 1H); 2.53–2.66(m, 2H); 3.18(dd,1H); 3.4(m,1H); 3.49(m, 1H); 3.55(m, 1H); 3.93(m, 2H); 4.15(dd, 1H); 7.35(s, 1H); 8.12(m, 1H): M/S+ve FAB(M+H)$^+$=508.

EXAMPLE 12: NMR: 1.03(t, 6H); 1.18(2s, 6H); 1.80(m, 1H); 2.70(m, 1H); 3.20(m, 6H); 3.45(m, 1H); 3.62(m, 2H), 4.05(m, 2H); 4.20(m, 1H); 7.20(s, 1H); 7.85(br, 1H): M/S+ve FAB(M+H)$^+$=599.

The starting materials for Examples 1 to 12 were prepared in the following general manner:

To a stirred solution of the appropriate 6-(1-hydroxyethyl)- 2-oxo-carbapenam-3-carboxylic acid ester or 6-(1-hydroxyethyl)-1-methyl- 2-oxocarbapenam-3-carboxylic acid ester (1 equivalent) and diisopropylethylamine (1.1 equivalents) in acetonitrile at 0° C., under an argon atmosphere, was added dropwise diphenyl chlorophosphate (1.1 equivalents). The solution was stirred at ambient temperature for 30 minutes to form the corresponding 3-diphenylphosphoryloxycarbapenem.

The solution was cooled to 0° and di-isopropylethylamine (1.5 equivalents) and the appropriate side-chain pyrrolidin-4-yl mercaptan (1.3 equivalents) in acetonitrile were added. The resultant solution was stirred at 0° C. for 90 minutes, solvent was removed by evaporation and the desired product isolated by medium pressure chromatography on silica (eluting with propan-2-ol/dichloromethane) to give an amorphous foam.

TABLE 2

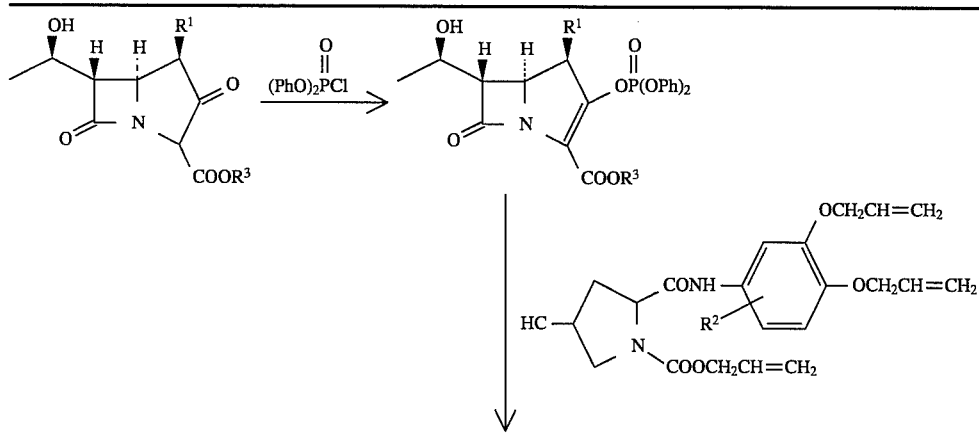

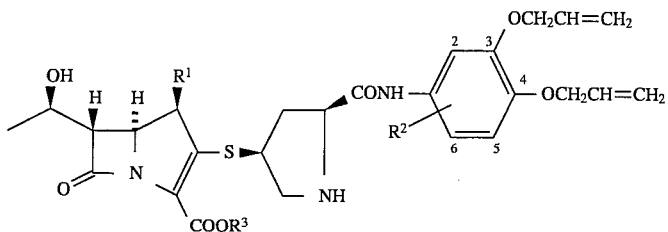

| Preparation of starting material for Example | R¹ | R² | R₃ | Footnotes |
|---|---|---|---|---|
| 1 | H | H | $CH_2-Ph-NO_2(p)$ | |
| 2 | $CH_3$ | 5-CN | $CH_2CH=CH_2$ | 1 |
| 3 | H | 5-Br | $CH_2CH=CH_2$ | |
| 4 | $CH_3$ | H | $CH_2CH=CH_2$ | |
| 5 | $CH_3$ | 5-$OCH_3$ | $CH_2CH=CH_2$ | 2 |
| 6 | $CH_3$ | 2,5-di-Cl | $CH_2CH=CH_2$ | 2 |
| 7 | $CH_3$ | 5-$OCH_2CH=CH_2$ | $CH_2CH=CH_2$ | 2,3 |
| 8 | $CH_3$ | 5-Br | $CH_2CH=CH_2$ | 2,3 |
| 9 | $CH_3$ | 5-CH=$NOCH_3$ | $CH_2CH=CH_2$ | 2,4 |
| 10 | $CH_3$ | 6-$COOCH_3$ | $CH_2CH=CH_2$ | 2,5 |
| 11 | $CH_3$ | 6-$COOCH_2CH=CH_2$ | $CH_2CH=CH_2$ | 1,3 |
| 12 | $CH_3$ | 6-$SO_2N(CH_2CH_3)_2$ | $CH_2CH=CH_2$ | 3,6 |

FOOTNOTES TO TABLE 2
1. Chromatography eluent: ethyl acetate.
2. Chromatography: gradient elution with acetonitrile/ethyl acetate.
3. Reaction for 16 hours at 0° C.
4. Reaction for 6 hours at 0° C. with warming to ambient.
5. Reaction for 72 hours at 0° C.
6. Chromatography: gradient elution ethyl acetate/hexane.

NMR and MS Data for Products of Table 2.
1. NMR(DMSO-$d_6$): 1.13(d, 3H); 1.88(m, 1H); 2.77(m, 1H); 3.3(partially obscured); 4.10(m, 6H); 4.48(m, 6H); 5.30(m, 8H); 6.02(m, 3H); 6.88(d, 1H); 7.07(d of d, 1H); 7.30(d, 1H); 7.69(d, 2H); 8.22(d, 2H): M/S+ve FAB(M+H)⁺ =749.
2. NMR: 1.12(2d, 6H); 1.90(partially obscured); 2.75(m, 1H); 3.22(d of d, 1H); 3.31(d of d, 1H); 3.50(m, 1H); 3.89(m, 1H); 3.97(m, 1H); 4.07(m, 1H); 4.22(m, 1H); 4.50(m, 9H); 5.27(m, 8H); 5.90(m, 4H); 7.48(s, 1H); 7.60(s, 1H): M/S+ve FAB(M+H)⁺=693.
3. NMR: 1.04(d, 3H); 1.90(partially obscured); 2.92(m, 1H); 3.23(m, 3H); 3.97(m, 5H); 4.43(m, 9H); 5.20(m, 8H); 5.83(m, 4H); 7.23(s, 1H); 7.42(s, 1H): M/S+ve FAB(M+H)⁺ =734.
4. NMR: 1.15(2d, 6H); 1.83(partially obscured); 2.73(m, 1H); 3.24(m, 1H); 3.51(m, 1H); 3.91(m, 2H), 4.10(m, 1H); 4.22(d, 1H); 4.50(m, 10H); 5.27(m, 8H); 5.90(m, 4H); 6.89(d, 1H); 7.08(d, 1H); 7.30(d of d, 1H): M/S+ve FAB(M+H)⁺=668.
5. NMR: 1.12(2d, 6H); 1.85(partially obscured); 2.74(m, 1H); 3.23(m, 2H); 3.50(m, 1H); 3.70(s, 3H); 3.86(m, 1H); 3.97(m, 1H); 4.08(d of d, 1H); 4.21(d, 1H); 4.43(m, 9H); 5.20(m, 8H); 5.90(m, 4H); 6.97(s, 2H): M/S+ve FAB(M+H)⁺=698.
6. NMR: 1.15(2d, 6H); 1.99(m, 1H); 2.79(m, 1H); 3.23(m, 1H); 3.31(m, 1H); 3.50(m, 1H); 3.91(m, 1H); 3.98(m, 1H); 4.08(m, 1H); 4.25(d of d, 1H); 4.54(m, 8H); 4.68(m, 1H); 5.1–5.4(m, 8H); 5.76–6.1(m, 4H); 7.69(br s, 1H): M/S+ve FAB(M+H)⁺=736.
7. NMR: 1.15(2d, 6H);, 1.85(partially obscured); 2.74(m, 1H); 3.22(d of d, 1H); 3.28(m, 1H); 3.50(m, 1H); 3.88(m, 1H); 3.99(m, 1H); 4.09(m, 1H); 4.20(d of d, 1H); 4.33–4.58(m, 10H); 4.65(m, 1H); 5.0–5.4(m, 10H); 5.7–6.09(m, 5H); 6.99(d, 2H): M/S+ve FAB(M+H)⁺ =724.
8. NMR: 1.14(2d, 6H); 1.89(partially obscured); 2.75(m, 1H); 3.23(dd, 1H); 3.3(m, 1H); 3.50(m, 1H); 3.89(m, 1H); 3.98(quintet, 1H); 4.08(m, 1H); 4.22(m, 1H); 4.32–4.59(m, 8H); 4.68(m, 1H); 5.14–5.42(m, 8H); 5.72–6.1(m, 4H); 7.32(s, 1H); 7.49(s, 1H): M/S+ve FAB(M+H)⁺=746/748.
9. NMR: (DMSO-$d_6$): 1.15(2d, 6H); 1.82(m, 1H); 2.75(m, 1H); 3.25(partially obscured); 3.55(m, 1H); 3.90(s, 3H); 3.95(m, 1H); 4.10(m, 1H); 4.22 (m, 1H); 4.35– 4.61(m, 8H); 4.69(m, 1H); 5.05(m, 1H); 5.18–5.45(m, 8H); 5.75–6.1(m, 4H); 7.22(m, 1H); 7.40(m, 1H); 8.25 (s, 1H); 10.05(br s, 1H).
10. NMR: 1.12(2d, 6H); 2.04(m, 1H); 2.82(m, 1H); 3.22(d of d, 1H); 3.45(m, 2H); 3.72(s, 3H); 3.98(m, 2H); 4.09(d of d, 1H); 4.25(dd, 1H); 4.39–4.65(m, 9H); 5.09–5.49(m, 8H); 5.68–6.1(m, 4H); 7.48(s, 1H); 8.35(d, 1H): M/S+ve FAB(M+H)⁺=726.
11. NMR: 1.12(d, 6H); 2.02(m, 1H); 2.81(m, 1H); 3.22(dd, 1H); 3.45(m, 2H); 3.99(m, 2H); 4.09(dd, 1H); 4.24(dd, 1H); 4.39–4.68(m, 10H); 4.75(dd, 1H); 5.1–5.49(m, 10H); 5.69–6.1(m, 5H); 7.5(s, 1H); 8.35(br d, 1H): M/S+ve FAB(M+H)⁺=752.
12. NMR: (DMSO-$d_6$): 0.98(m, 6H); 1.15(m, 6H); 2.00(m, 1H; 2.80(m, 1H); 3.15(m, 4H); 3.25(m, 1H); 3.50(m, 1H); 3.95(m, 2H); 4.20(m, 2H); 4.40–4.70(m, 9H); 5.05–5.50(m, 9H); 5.70–6.10(m, 4H); 7.19(s, 1H); 8.15(br.d, 1H); 10.1(br d, 1H): M/S+ve FAB(M+H)⁺=803.

Esters of 6-(1-hydroxyethyl)-2-oxocarbapenam carboxylic acid and 6-(1-hydroxyethyl)-1-methyl-2-oxocarbapenam carboxylic acid are well known in the literature, see for example EP-A-126780 and EP-A-208889.

We prefer to prepare allyl 6-(1-hydroxyethyl)-1-methyl-2-oxocarbapenam carboxylate in situ from allyl 2-diazo-3-oxo-4-methyl-4-( 3-(1-hydroxyethyl)-2-oxoazetidin-4yl)butanoate and rhodium octanoate (see for example EP-A-341557 and Tet. Lett. 1988, 29, 61).

PREPARATION OF SIDE CHAIN PYRROLIDIN-4-YL MERCAPTANS

The side-chain pyrrolidin-4-yl mercaptans were prepared in the following general manner:

4-Acetylthio-1-allyloxycarbonyl-2-carboxypyrrolidine (1 equivalent) was treated with oxalyl chloride (2 equivalents)

in dichloromethane in the presence of a small amount of DMF. The reaction mixture was stirred at ambient temperature for 30 minutes, a further drop of DMF was added, and stirring was continued for a further 20 minutes. The mixture was evaporated (azeotroping with toluene) and filtered to remove Vilsmeier reagent. The resultant acid chloride was dissolved in THF and added dropwise to the appropriate aniline (generated in situ from the corresponding hydrochloride) in THF in the presence of diisopropylethylamine. The mixture was stirred for 60–150 minutes at 0° C., under argon, diluted with ethyl acetate, washed ($H_2O$, 2N HCl, $H_2O$, saturated $NaHCO_3$), evaporated and subjected to medium pressure chromatography with ethyl acetate/hexane to give the corresponding 4-acetylthio-1-allyloxycarbonyl-2-(3,4-diallyloxyphenylcarbamoyl)pyrrolidine (compound C).

The 4-acetylthio compound was dissolved in methanol and the solution flushed with argon. 1N Sodium hydroxide (1.1–1.5 equivalents) was added and the mixture was stirred at ambient temperature for 60 minutes. 2N Hydrochloric acid (1.1–1.5 equivalents) was added, methanol removed by evaporation and the residue partitioned between ethyl acetate and water. The organic layer was washed with brine, dried ($MgSO_4$) and evaporated to give the corresponding 1-allyloxycarbonyl-2-(3,4-diallyloxyphenylcarbamoyl)-pyrrolidin- 4-yl thiol (compound D) as a gum.

Thus the following compounds were prepared according to the following Schemes:

7.32(d, 1H); 7.50(d, 1H); 10.05(s, 1H).
R=2,5-di-Cl (DMSO-$d_6$) 1.88(m, 1H); 2.72(m, 1H); 3.01(dd, 1H); 3.38(m, 1H); 3.95(m, 1H); 4.42–4.6(m, 7H); 5.08–5.45(m, 6H); 5.75–6.15(m, 3H); 7.6(br d, 1H); 9.62(br s, 1H): M/S+ve FAB(M+H)$^+$=487.
R=5-OCH$_2$CH=CH$_2$ (DMSO-$d_6$) 1.80(m, 1H); 2.68(m, 1H); 3.08(m, 1H); 3.38(partially obscured); 3.95(m, 1H); 4.24–4.55(m, 9H); 5.02–5.48(m, 8H); 5.9–6.15(m, 4H); 6.99(d, 2H); 9.91(br s, 1H).
R⊙5-CH=NOCH$_3$ 1.8(partially obscured); 2.70(m, 1H); 3.22(m, 1H); 3.38(m, 1H); 3.90(s, 3H); 3.98(partially obscured); 4.32(m, 1H); 4.45–4.6(m, 6H); 5.15–5.5(m, 6H); 5.85–6.18(m, 3H); 7.55(m, 2H); 8.30(s, 1H).
R=6-CO$_2$CH$_3$ NMR (at 80° C.) 2.24(m, 1H); 2.72(m, 1H); 3.6(m, 2H); 3.84(d, 3H); 4.02(m, 1H); 4.36–4.68(m, 7H); 5.06–5.5(m, 6H); 5.78–6.18(m, 3H); 7.53(d, 1H); 8.32(d, 1H): M/S+ve FAB(M+H)$^+$=477.
R=6 COOCH$_2$CH=CH$_2$ NMR 1.91(m, 1H); 2.72(m, 2H); 3.43(m, partially obscured); 3.90(m, 1H); 4.04(m, 1H); 4.33(m, 1H); 4.42–4.82(m, 8H); 5.0–5.52(m, 9H); 5.72–6.18(m, 4H); 7.49(d, 1H); 8.3(m, 1H): M/S+ve FAB(M+H)$^+$=503.
[The hydrolysis of this compound was performed using allyl alcohol as solvent].
R=6-SO$_2$N(CH$_2$CH$_3$)$_2$ NMR (DMSO-$d_6$): 0.99(m, 6H); 2.19(m, 1H); 2.71(m, 1H); 3.00–3.56(m, 6H); 3.72(m, 1H); 3.98(m, 1H); 4.30–4.65(m, 7H); 5.10–5.51(m, 6H); 5.64–6.15(m, 3H); 7.18(d, 1H); 8.20(br, 1H); 10.1(br, 1H):

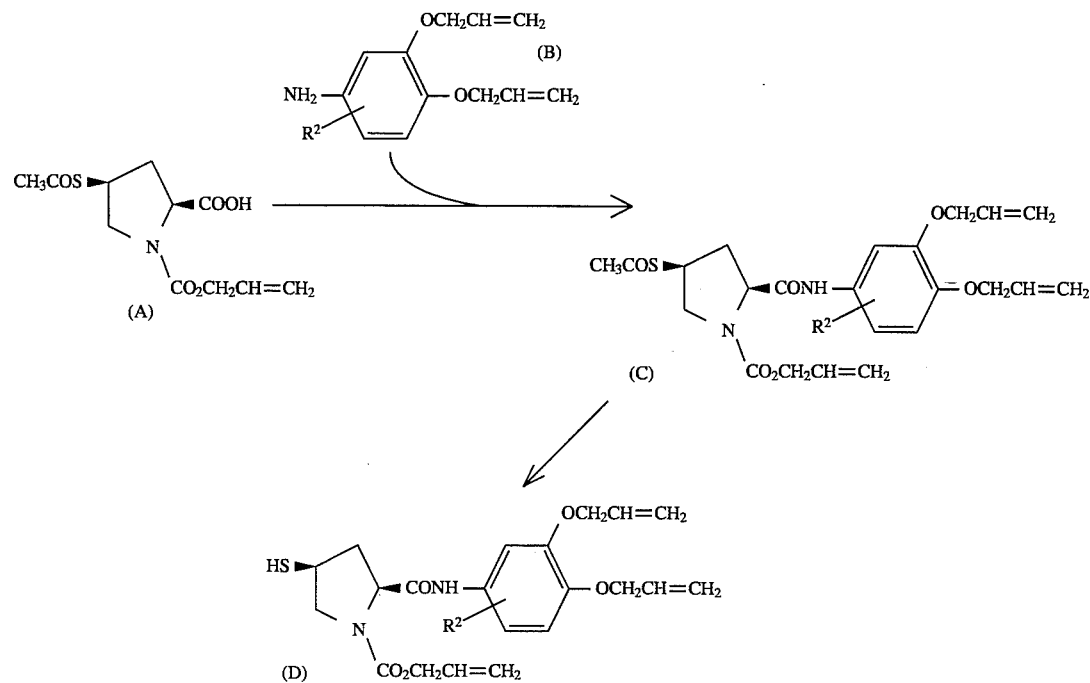

Scheme A

NMR and MS Data for compounds (D).
R=H (CDCl$_3$) 1.88(d, 1H); 2.47(br s, 1H); 2.64(br s, 1H); 3.36(m, 2H); 4.07(m, 1H); 4.47(t, 1H); 4.59(m, 6H); 5.32(m, 6H); 5.99(m, 3H); 6.81(d, 1H); 6.88(d of d, 1H); 7.32(d, 1H); 8.71 (br s, 1H): M/S+ve FAB(M+H)$^+$=419.
R=5-Br (DMSO-$d_6$) 1.79(d, 1H); 2.68(m, 1H); 3.05(m, 1H); 3.2(partially obscured); 3.95(m, 1H); 4.28(m, 1H); 4.42–4.6(m, 6H); 5.0–5.48(m, 6H); 5.69–6.17(m, 3H);

M/S+ve FAB(M+H)$^+$=554.
Compounds D wherein R=5-CN and 5-CH$_3$ were prepared and utilised in situ without characterisation.
NMR and MS Data for Compounds (C)
R=H (CDCl$_3$) 2.32(s, 3H); 2.58(br s, 2H); 3.36(q, 1H); 4.06(m, 2H); 4.58(m, 7H); 5.32(m, 6H); 6.00(m, 3H); 6.81(d, 1H); 6.90(d of d, 1H); 7.32(d, 1H); 8.85(br s, 1H): M/S+ve FAB(M+H)$^+$=461.

R=5-Br (DMSO-d$_6$) 1.88(m, 1H); 2.34(s, 3H); 2.76(m, 1H); 3.25(partially obscured); 3.98(m, 2H); 4.35(m, 1H); 4.45–4.6(m, 6H); 5.02–5.49(m, 6H); 5.72–6.18(m, 3H); 7.3(d, 1H); 7.5(d, 1H); 10.05(br s, 1H).

R=2,5-di-Cl (DMSO-d$_6$) 1.94(m, 1H); 2.33(s, 3H); 2.76(m, 1H); 3.99(m, 2H); 4.55(m, 7H); 5.05–5.45(m, 7H); 5.78–6.18(m, 3H); 7.59(br d, 1H); 9.68(br s, 1H): M/S+ve FAB(M+H)$^+$=529.

R=5-OCH$_2$CH=CH$_2$ (DMSO-d$_6$) 1.85(m, 1H); 2.32(s, 3H); 2.75(m, 1H); 4.0(m, 2H); 4.3–4.58(m, 9H); 5.02–5.48(m, 9H); 5.7–6.15(m, 4H); 6.98(s, 2H); 9.91(s, 1H).

R=5-CH=NOCH$_3$ (DMSO-d$_6$) 1.88(m, 1H); 2.32(s, 3H); 2.75(m, 1H); 3.32(partially obscured); 3.9(m, 2H); 4.0(m, 2H); 4.3–4.59(m, 7H); 5.02–5.49(m, 6H); 5.75–6.17(m, 3H); 7.45(d, 1H); 7.54(br d, 1H); 8.28(s, 1H); 10.05(s, 1H).

R=6-COOCH$_2$CH=CH$_2$ (DMSO-d$_6$) 1.95(m, 1H); 2.32(s, 3H); 2.78(m, 1H); 3.25 and 3.96 (partially obscured); 4.3(m, 1H); 4.4–4.85(m, 8H); 5.1–5.5(m, 8H); 5.8–6.15(m, 4H); 7.52(s, 1H); 8.3(br s, 1H).

R=5-CN (CDCl$_3$) 2.34(s, 3H); 2.50(m, 2H); 3.39(q, 1H); 4.08(m, 2H); 4.58(m, 7H); 5.32(m, 6H); 6.00(m, 3H); 7.14(d, 1H); 7.53(d, 1H); 9.38(br s, 1H): M/S+ve FAB(M+H)$^+$=486.

R=5-OCH$_3$ (CDCl$_3$) 2.33(s, 3H); 2.53(m, 2H); 3.37(q, 1H); 3.82(s, 3H); 4.07(m, 2H); 4.50(m, 5H); 4.66(d, 2H); 5.27(m, 6H); 6.00(m, 3H); 6.81(s, 2H); 9.04(br s, 1H): M/S+ve FAB(M+H)$^+$=491.

R=6-SO$_2$N(CH2CH$_3$)$_2$ (DMSO-d$_6$): 1.00(t, 6H); 2.03(m, 1H); 2.32(s, 3H); 2.79(m, 1H); 3.14–3.32(m, partially obscured); 4.05(m, 2H); 4.40–4.65(m, 7H); 5.16–5.50(m, 6H); 5.80–6.15(m, 3H); 7.19(s, 1H); 8.15(br s, 1H); 10.10(br s, 1H): M/S+ve FAB(M+H)$^+$=596.

Compound (A)

4-Acetylthio-1-allyloxycarbonylpyrrolidine-2-carboxylic acid was prepared as follows:

a) To a solution of 4-hydroxyproline (0.25M) in 4N sodium hydroxide (78ml), at 0°–5° C., was added allyl chloroformate (0.31M) in dioxan (156 ml) and 4N sodium hydroxide (78 ml). The dioxan solution and sodium hydroxide were added simultaneously, in batches, allowing the temperature to return to below 5° C. after each addition. The mixture was stirred for a further hour, washed with ethyl acetate, acidified (conc. HCl) and extracted into ethyl acetate. The organic phase was washed with brine, dried and evaporated to give 1-allyloxycarbonyl-4-hydroxypyrrolidine-2-carboxylic acid as a viscous syrup. This (0.1M) was treated with 4-methoxybenzyl chloride (0.19M) and triethylamine (0.2M) in DMF (200 ml), under argon, at 70° C. for 10 hours. Ethyl acetate was added and the mixture was washed with water and brine and evaporated to give a gum. This was subjected to medium pressure chromatography (gradient elution with ether to ether/1% methanol) to give 4-methoxybenzyl 1-allyloxycarbonyl-4-hydroxy-pyrrolidine- 2-carboxylate.

b) To a solution of the product from (a) (0.066M) and triphenylphosphine (0.099M) in THF (200 ml) at 0° C., under argon, was slowly added diethylazodicarboxylate (0.099M) in THF (60 ml). The solution was stirred for 30 minutes at 0° C. Thiolacetic acid (0.099M) in THF (60 ml) was slowly added and the resultant mixture was stirred for 1 hour at 0° C., for 18 hours at ambient, evaporated and subjected to medium pressure chromatography (ethyl acetate/hexane gradient elution) to give 4-methoxybenzyl 4-acetylthio-1-allyloxycarbonyl-pyrrolidine- 2-carboxylate.

c) To the product from (b) above (0.056M) was added anisole (0.112M) in trifluoroacetic acid (60 ml) at ambient temperature. The mixture was stirred for 15 minutes, evaporated, and the residue was dissolved in ether (150 ml) and treated with cyclohexylamine (0.056M) in ether (50 ml). The cyclohexylamine salt of 4-acetylthio- 1-allyloxy-carbonylpyrrolidine-2-carboxylic acid crystallised out and was collected: NMR (CDC$_{13}$) 2.0(m, 1H); 2.30(s, 3H); 2.56(m, 1H); 3.32(dd, 1H); 3.91(m, 1H); 4.05(dd, 1H); 4.16(t, 1H); 4.53(m, 2H); 5.20(m, 2H); 5.90(m, 1H); 6.68(br s, 3H) and cyclohexylamine peaks at 1.0–2.0 and 2.95: M/S C.I.(M+H)$^+$=274.

Compounds (B) in Examples 1–11

Compounds (B) in examples 1–11 were prepared according to the following Scheme:

Scheme B

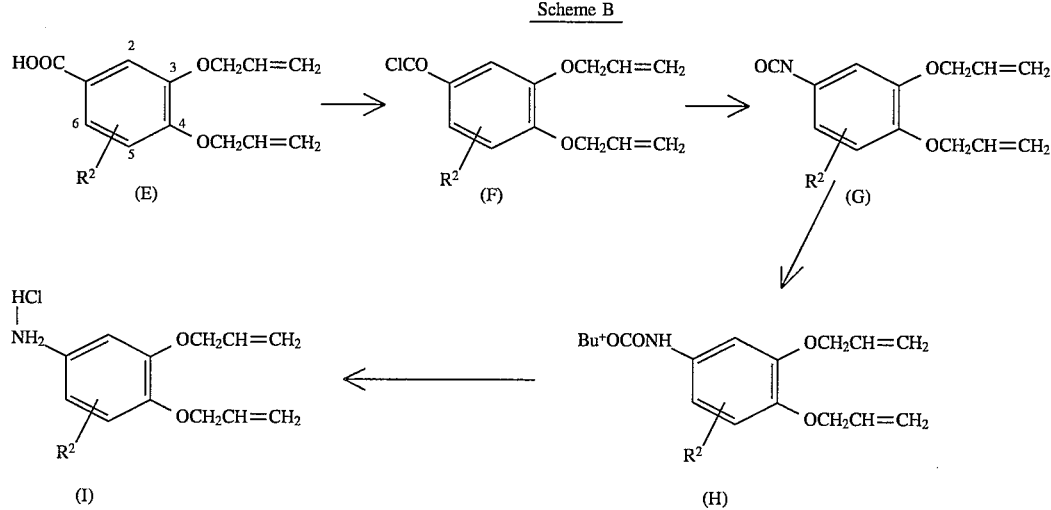

General method of preparation of Compounds (I):

Acid (E) (1.73 mmol) in dichloromethane (5 ml) was treated with oxalyl chloride (2.59 mmol) and DMF (one drop). The mixture was stirred, under argon, for 30 minutes at room temperature. Further DMF (one drop) was added, the mixture stirred for a further 30–60 minutes, evaporated (azeotroping with toluene), dissolved in toluene, filtered and evaporated to afford the acid chloride (F).

The acid chloride (F) (1.73 mmol) and trimethylsilyl azide (2.59 mmol) were heated at reflux in toluene (5 ml) for 3–18 hours. The mixture was evaporated to give the isocyanate (G) as an oil which was used without purification. The isocyanate (1.73 mmol) was heated at reflux in t-butanol (5 ml) for ½–3 hours, evaporated and subjected to medium pressure chromatography (ethyl acetate/hexane) to give compound (H). This was dissolved in a minimum amount of ethyl acetate and treated with ethyl acetate saturated with HCl to give the aniline hydrochloride (I) as a precipitate.

All reactions were followed by thin layer chromatography.

NMR data for Compounds (I)

$R^2$=2,5-di-Cl (DMSO-$d_6$) 4.39(m, 2H); 4.52(m, 2H); 5.19–5.44(m, 4H); 5.95–6.15(m, 2H); 6.68(s, 1H): M/S(M+H)$^+$=274.

$R^2$=5-OCH$_2$CH=CH$_2$ (DMSO-$d_6$) 4.44(m, 2H); 4.55(m, 4H); 5.12–5.49(m, 6H); 5.91–6.15(m, 3H); 6.65(s, 2H).

$R^2$=5-CH=NOCH$_3$(DMSO-$d_6$) 3.92(s, 3H); 4.5(dt, 2H); 5.2–5.5(m, 4H); 5.92–6.19(m, 2H); 7.02(d, 1H); 7.19(d, 1H); 8.29(s, 1H).

$R^2$=H (DMSO-$d_6$) 4.56(m, 4H); 5.33(m, 4H); 6.06(m, 2H); 6.90(d of d, 1H); 7.03(d, 1H); 7.08(d, 1H).

$R^2$=5-Br (DMSO-$d_6$) 4,48(m, 2H); 4.61(m, 2H); 5.32(m, 4H); 6.05(m, 2H); 6.92(d, 1H); 7.03(d, 1H).

$R^2$=5-CN (DMSO-$d_6$) 4.62(m, 4H); 5.32(m, 4H); 6.03(m, 2H); 6.97(d, 1H); 7.16(d, 1H): C.I.(M+H)$^+$=231.

$R^2$=5-OCH$_3$ (DMSO-$d_6$) 3.78(s, 3H); 4.42(m, 2H); 4.57(m, 2H); 5.80(m, 4H); 6.02(m, 2H); 6.69(s, 2H): C.I.(M+H)$^+$=236.

$R^2$=6-COOCH$_2$CH=CH$_2$ (DMSO-$d_6$) 4.45–4.78(3d, 6H); 5.2–5.5(m, 6H); 5.92–6.16(m, 3H); 6.72(s, 1H); 7.32(s, 1H): M/S(M+H)$^+$=290.

[This compound was prepared by acetylating 2-amino-4,5-dimethoxybenzoic acid to form 2-acetamido-4,5-dimethoxybenzoic acid; removing the methoxy groups with BBr$_3$; alkylating with allyl bromide and hydrolysing the acetamido group with conc. HCl in methanol]

Preparation of Acids (Compounds (E))

3,4-Diallyloxy-5-bromobenzoic acid was prepared as follows:

Methyl 3,4-dihydroxy-5-bromobenzoate (49 g, see Chem. Abs., 89:2327 g) and K$_2$CO$_3$ (92 g) were placed in a flask in acetone (500 ml). Allyl bromide (49 ml) was slowly added to the mixture, which was stirred at room temperature for 5 days. After filtration, solvent was evaporated, the residue taken up in ethyl acetate, washed with water, and dried (MgSO$_4$). Evaporation of the solvent gave methyl 3,4-diallyloxy-5-bromobenzoate (65 g): NMR (DMSO-$d_6$) 3.86 (s, 3H); 4.67 (m, 4H); 5.20–5.53 (m, 4H); 5.95–6.19 (m, 2H); 7.54 (d, 1H); 7.73 (d, 1H).

Crude ester (65 g) was dissolved in methanol (400 ml), and treated with aqueous sodium hydroxide (40 ml, 10.5N). After reflux overnight, methanol was evaporated, the aqueous residue diluted with water, and acidified with conc. HCl. The white precipitate was filtered off, and dissolved in ethyl acetate. A water layer was separated, and the organic layer dried over MgSO$_4$. Filtration and evaporation gave as a white solid 3,4-diallyloxy-5-bromobenzoic acid (59 g): NMR (CDCl$_3$) 4.67 (m, 4H); 5.42–5.51 (m, 4H); 6.00–6.21 (m, 2H); 7.56 (d, 1H); 7.94 (d, 1H), 11.33 (s, 1H).

2,5-Dichloro-3,4-diallyloxybenzoic acid was prepared as follows:

2,5-Dichloro-3,4-dihydroxybenzoic acid (10.7 g, see J. Antibiotics, 1987, 40, 22) and K$_2$CO$_3$ (33.1 g) were suspended in DMF (150 ml), and treated with allyl bromide (14.7 ml). After stirring overnight, the mixture was filtered, diluted with ethyl acetate, washed with sodium bicarbonate, dried (MgSO$_4$), filtered and evaporated to give allyl 2,5-dichloro-3,4-diallyloxybenzoate (14.7 g): NMR (CDCl$_3$) 4.55–4.65 (m, 4H); 4.82 (m, 2H); 5.24–5.50 (m, 6H); 5.94–6.22 (m, 3H); 7.70 (s, 1H).

Crude ester was hydrolysed as for the methyl ester above, to give 2,5-dichloro-3,4-diallyloxybenzoic acid (12 g): NMR (DMSO-$d_6$) 4.55–4.68 (m, 4H); 5.23–5.48 (m, 4H); 6.00–6.20 (m, 2H); 7.69 (s, 1H).

3,4,5-Triallyloxybenzoic acid was prepared as follows.

Ethyl gallate (7.92 g, commercially available, Fluka), and K$_2$CO$_3$ (27.6 g) in DMF (40 ml) were treated with allyl bromide (13.5 ml) as above, to give ethyl 3,4,5-triallyloxybenzoate (14 g): NMR (CDCl$_3$) 1.49 (t, 3H); 4.35 (q, 2H); 4.62 (m, 6H); 5.15–5.48 (m, 6H); 6.00–6.28 (m, 3H); 7.29 (s, 1H). This crude ester was hydrolysed essentially as above to give 3,4,5-triallyloxybenzoic acid(10.4 g): NMR (CDCl$_3$) 4.64 (m, 6H); 5.15–5.51 (m, 6H); 6.00–6.20 (m, 3H); 7.35 (s, 1H).

3,4-Diallyloxy-5-cyanobenzoic acid was prepared as follows:

3,4-Dihydroxy-5-cyanobenzoic acid, (see GB 2 200 109) was converted, essentially as above, to allyl 3,4-diallyloxy-5-cyanobenzoate: NMR (CDCl$_3$) 4.63 (m, 2H); 4.77–4.87 (m, 4H); 5.23–5.51 (m, 6H); 5.92–6.18 (m, 3H); 7.76 (d, 1H); 7.86 (d, 1H). This ester was hydrolysed as above to give 3,4-diallyloxy-5-cyanobenzoic acid: (DMSO-$d_6$) 4.72–4.84 (m, 4H); 5.23–5.51 (m, 4H); 5.93–6.18 (m, 2H); 7.79 (s, 2H).

3,4-Diallyloxy-5-methoxybenzoic acid was prepared as follows:

3,4-Dihydroxy-5-methoxybenzoic acid (50 mM), K$_2$CO$_3$ (300 mM) and allyl bromide (200 mM) in DMF (100 ml) was stirred vigorously at 80° C. for 2½ hours. The mixture was filtered and the filtrate partitioned between ethyl acetate and water. The organic phase was washed with brine and evaporated to give allyl 3,4-diallyloxy-5-methoxybenzoate as a crude oil: NMR (CDCl$_3$) 3.89(s, 3H); 4.61(m, 4H); 4.82(m, 2H); 5.31(m, 6H); 6.06(m, 3H); 7.32(s, 2H).

The ester was hydrolysed with KOH in water at 100° C. for 45 minutes to afford 3,4-diallyloxy-5-methoxybenzoic acid, after chromatography, as a waxy solid; NMR (DMSO-$d_6$) 3.68(s, 3H); 4.43(d of d, 4H); 5.21(m, 4H); 5.95(m, 2H); 7.22(s, 2H).

3,4-Diallyloxy-5-methoxyiminomethylbenzoic acid was prepared as follows:

2,3-Dihydroxy-5-carboxybenzaldehyde (GB-A-2200109) was alkylated with allyl bromide, as above, to give the corresponding tri-allyl derivative. This was treated with O-methylhydroxylamine hydrochloride and pyridine in ethanol at reflux to give allyl 3,4-diallyloxy-5-methoxyiminomethylbenzoate which was hydrolysed with KOH in aqueous ethanol at reflux to give 3,4-diallyloxy-5-methoxyiminomethylbenzoic acid; NMR (DMSO-$d_6$) 3.92(s, 3H); 4.61(m, 2H); 4.7(m, 2H); 5.2–5.5(m, 4H); 5.94–6.18(m, 2H); 7.56(d, 1H); 7.92(d, 1H); 8.32(s, 1H); 12.9(s, 1H).

Compound (B) in Example 12.

Condensed diethylamine (4.8 ml) was slowly added to a solution of 4,5-dimethoxy-2-nitrobenzenesulphonyl chloride*. The reaction mixture was stirred for 1 hour at 0° C. and then heated on a steam bath for 10 minutes. The reaction was chilled, filtered and the solvent evaporated. The di-[N-ethyl]-4,5-dimethoxy-2-nitrobenzenesulphonamide thus prepared was purified by sinter flash chromatography eluting with dichloromethane (50%). NMR (DMSO-$d_6$): 1.09(t, 6H); 3.32(m, 4H); 3.95(2xs, 6H); 7.25(s, 1H); 7.59(s, 1H): M/S CI(M+H)$^+$=319.

* [4,5-dimethoxy-2-nitrobenzenesulphonyl chloride was prepared according to J. Med. Chem., 11, 136, (1968).]

The sulphonamide prepared above (5.78 mmol) and tin (II) chloride dihydrate (29 mmol) were added to ethyl acetate (40 ml). The reaction mixture was stirred for 1.5 hours at 60° C. and then poured into ice and basified with an aqueous solution of sodium hydroxide. A precipitate formed which was filtered off and the product extracted from the aqueous phase with ethyl acetate. This extract was dried (MgSO$_4$) and the solvent evaporated to give di-[N-ethyl]-4,5-dimethoxy- 2-aminobenzenesulphonamide which was used without further purification.

The aniline prepared above (5.78 mmol) was stirred in acetic anhydride (20 ml) at 0° C. After 2 hours the solution was poured into ice and the product extracted with ethyl acetate. This extract was washed with a saturated aqueous solution of sodium hydrogen carbonate, dried (MgSO$_4$) and the solvent evaporated to give 4,5-methoxy-2-acetylaminodi-[N-ethyl]benzenesulphonamide (95%). NMR (DMSO-d$_6$): 1.01(t, 6H); 2.09(s, 3H); 3.19(m, 4H); 3.80(s, 6H); 7.25(s, 1H); 7.60(s, 1H); 9.26(br s, 1H): M/S CI NH$_3$(M+H)$^+$=331.

Boron tribromide (2.22 mmol) was added to a solution of the acylated aniline prepared above (0.54 mmol) in dichloromethane (3 ml). The reaction mixture was stirred for 4 hours before being quenched by the addition of crushed ice. A 2N aqueous solution of sodium hydroxide was added and the organic and aqueous phases separated. The aqueous phase was acidified with a 2N aqueous solution of hydrochloric acid and extracted with ethyl acetate. This was dried (MgSO$_4$) and evaporated to give 4,5-dihydroxy-2-acetylamino di-[N-ethyl]benzenesulphonamide (95%). NMR (DMSO-d$_6$): 1.00(t, 6H); 2.05(s, 3H); 3.15(m, 4H); 7.14(s, 1H); 7.44(s, 1H); 9.06(br s, 1H); 9.39(br s, 1H); 10.00(br s, 1H): M/S CI NH$_3$ (M+H)$^+$=303.

Potassium carbonate (2.6 mmol) was added to a solution of the diol prepared above (0.52 mmol) in DMF (2 ml). Allyl bromide (2 mmol) in DMF (1 ml) was added dropwise to the reaction mixture and stirred for 5 hours. The mixture was left for 20 hours unstirred and filtered to remove the potassium carbonate. The filtrate was partitioned between ethyl acetate and water. The organic phase was washed with brine, an aqueous solution of sodium hydrogen carbonate and brine again. The organic phase was dried (MgSO$_4$) and the solvent evaporated to give 4,5-diallyloxy-2-acetylaminodi-[N-ethyl]benzenesulphonamide (80%). NMR (DMSO-d$_6$): 1.00(t, 6H); 2.09(s, 3H); 3.19(m, 4H); 4.60(m, 4H); 5.22–5.55(m, 4H); 5.92–6.16(m, 2H); 7.24(s, 1H); 7.65(s, 1H); 9.25(s, 1H): M/S CI NH$_3$(M+H)$^+$=383.

A mixture of the diallyloxybenzenesulphonamide compound from the above reaction (0.42 mmol), concentrated hydrochloric acid (0.5 ml), water (4.4 ml) and methanol (3 ml) were heated at reflux for 3 hours. The solvents were evaporated and the residue dried under a high vacuum to give 4,5-diallyloxy-2-aminodi-[N-ethyl]benzenesulphonamide (88%). NMR (DMSO-d$_6$): 1.01(t, 6H); 3.15(m, 4H); 4.15(br, partially obscured, 2H); 4.42(m, 2H); 5.18–5.50(m, 4H); 5.89–6.15(m, 2H); 6.48(s, 1H); 6.95(s, 1H): M/S CI NH$_3$(M+H)$^+$=341.

We claim:

1. A carbapenem compound of the formula (I)

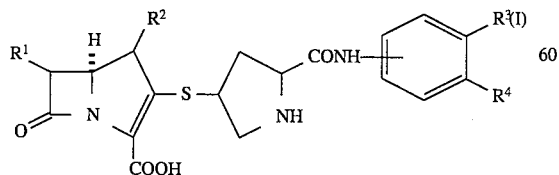

$R^1$ is 1-hydroxyethyl, 1-fluoroethyl or hydroxymethyl;

$R^2$ is hydrogen or $C_{1-4}$alkyl;

$R^3$ and $R^4$ are ortho with respect to one another wherein $R^3$ and $R^4$ are independently hydroxy or in vivo hydrolysable esters thereof;

the benzene ring being optionally further substituted by $C_{1-4}$alkyl, halo, hydroxy, hydroxy$C_{1-4}$alkyl, amino, nitro, $C_{1-4}$alkoxy, carboxy$C_{1-4}$alkyl, $C_{1-4}$alkanoylamino, N-alkyl-N-$C_{1-4}$alkanoylamino, trifluomethyl, carboxy, carbamoyl, $C_{1-4}$alkylcarbamoyl, di-$C_{1-4}$alkylcarbamoyl, cyano, $C_{1-4}$alkanesulphonamido, $C_{1-4}$alkanoyl, $C_{1-4}$alkanoyloxy, $C_{1-4}$alkoxycarbonyl, $C_{1-4}$alkylthio, $C_{1-4}$alkanesulphinyl, $C_{1-4}$alkanesulphonyl, $C_{2-4}$alkenyl, hydroxyiminomethyl, $C_{1-4}$alkoxyiminomethyl, aminosulphonyl, $C_{1-4}$alkylaminosulphonyl or di-[N-$C_{1-4}$alkyl]aminosulphonyl;

or a pharmaceutically acceptable salt or in vivo hydrolysable ester thereof.

2. A compound according to claim 1 wherein $R^1$ is 1-hydroxyethyl.

3. A compound according to claim 1 wherein $R^2$ is hydrogen.

4. A compound according to the claim 1 wherein the benzene ring is optionally further substituted by fluoro, bromo, chloro, cyano, nitro, carboxymethyl, hydroxy, di-[N-methyl]carbamoyl, methanesulphonyl, di-[N-ethyl]aminosulphonyl or methoxycarbonyl.

5. A compound according to claim 1 of the formula (IV):

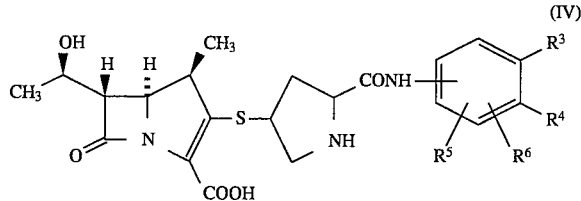

wherein $R^3$ and $R^4$ are as defined in claim 1 and $R^5$ and $R^6$ are independently hydrogen, halo, cyano, nitro, carboxy, carboxymethyl, methanesulphonyl, di-[N-methyl]carbamoyl, di-[N-ethyl]aminosulphonyl or hydroxy.

6. A compound according to claim 1 wherein the benzene ring is substituted by $R^3$ and $R^4$ in positions 3 and 4 relative to the amido linking group.

7. A compound 1 selected from the group consisting of (5R, 6S, 8R, 2' S, 4' S)-2-(2-(3,4-dihydroxyphenylcarbamoyl)pyrrolidin- 4-ylthio)-6-(1-hydroxyethyl)carbapenem-3-carboxylic acid;

(1R,5R,6S,8R,2'S,4'S)-2-(2-(5-cyano- 3,4-dihydroxyphenylcarbamoyl)pyrrolidin-4-ylthio)-6-(1-hydroxyethyl)-1-methylcarbapenem- 3-carboxylic acid;

(5R,6S,8R,2'S,4'S)-2-(2-(5-bromo- 3,4-dihydroxyphenylcarbamoyl)pyrrolidin-4-ylthio)-6-(1-hydroxyethyl)carbapenem-3-carboxylic acid;

(1R,5R,6S,8R,2'S,4 ' S)-2-(2-(3,4-dihydroxyphenylcarbamoyl)pyrrolidin- 4-ylthio)-6-(1-hydroxyethyl)-1-methylcarbapenem-3-carboxylic acid;

(1R,5R,6S,8R,2'S,4'S)-2-(2-(5-methoxy- 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(2,5-dichloro- 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(5-hydroxy- 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(5-bromo- 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(5-N-methoxyiminomethyl-3,4-dihydroxyphenylcarbamoyl)pyrrolidin-4-ylthio)-6-(1-hydroxyethyl)- 1-methylcarbapenem-3-carboxylic acid; p1 (1R,5R,6S,8R,2'S,4'S)-2-(2-(6-methoxycarbonyl- 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(6-carboxy- 3,4-dihydroxyphenylcarbamoyl)pyrrolidin-4-ylthio)-6-(1-hydroxyethyl)-1-methylcarbapenem- 3-carboxylic acid; and (1R,5R,6S,8R,2'S, 4'S)-2-(2-(6-di-(N-ethyl)aminosulphonyl- 3,4-dihydroxyphenylcarbamoyl)pyrrolidin-4-ylthio)-6-(1-hydroxyethyl)- 1-methylcarbapenem-3-carboxylic acid;

or a pharmaceutically acceptable salt or in vivo hydrolysable ester thereof.

8. An antibacterial pharmaceutical composition which comprises an antibacterially effective amount of a compound according to claim 1 and a pharmaceutically acceptable carrier.

9. A compound according to claim 1 in the form of a sodium salt.

10. An antibacterial pharmaceutical composition which comprises a pharmaceutically effective amount of a compound according to claim 5 and a pharmaceutically acceptable carrier.

11. An antibacterial pharmaceutical composition which comprises an antibacterially effective amount of a compound according to claim 7 and a pharmaceutically acceptable carrier.

12. A method of treatment of a bacterial infection in a human or other mammal in need thereof by administering an antibacterially effective amount of a carbapenem compound of the formula

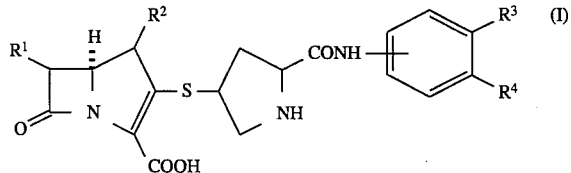

wherein:

$R^1$ is 1-hydroxyethyl, 1-fluoroethyl or hydroxymethyl;

$R^2$ is hydrogen or $C_{1-4}$alkyl;

$R^3$ and $R^4$ are ortho with respect to one another wherein $R^3$ and $R^4$ are independently hydroxy or an in vivo hydrolysable ester thereof;

the benzene ring being optionally further substituted by $C_{1-4}$alkyl, halo, hydroxy, hydroxy$C_{1-4}$alkyl, amino, nitro, $C_{1-4}$alkoxy, carboxy$C_{1-4}$alkyl, $C_{1-4}$alkanoylamino, N-alkyl-N-$C_{1-4}$alkanoylamino, trifluoroethyl, carboxy, carbamoyl, $C_{1-4}$alkylcarbamoyl, di-$C_{1-4}$alkylcarbamoyl, cyano, $C_{1-4}$alkanesulphonamido, $C_{1-4}$alkanoyl, $C_{1-4}$alkanoyloxy, $C_{1-4}$alkoxycarbonyl, $C_{1-4}$alkylthio, $C_{1-4}$alkanesulphinyl, $C_{1-4}$alkanesulphonyl, $C_{2-4}$alkenyl, hydroxyiminomethyl, $C_{1-4}$alkoxyiminomethyl, aminosulphonyl, N-$C_{1-4}$alkylaminosulphonyl or di-[N-$C_{1-4}$alkyl]aminosulphonyl;

or a pharmaceutically acceptable salt or in vivo hydrolysable ester thereof, to a patient in need thereof.

13. A method of treatment of a bacterial infection in a human or other mammal in need thereof by administering an antibacterially effective amount of a carbapenem compound of the formula (IV):

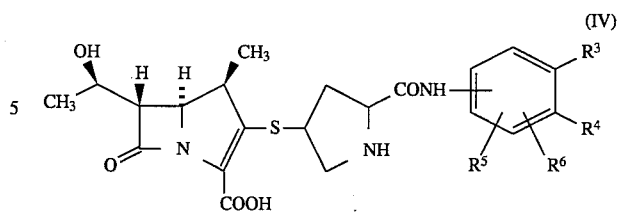

wherein $R^3$ and $R^4$ are ortho with respect to one another wherein $R^3$ and $R^4$ are independently hydroxy or an in vivo hydrolysable ester thereof; and $R^5$ and $R^6$ are independently hydrogen, halo, cyano, nitro, carboxy, carboxymethyl, methanesulphonyl, di-[N-methyl]carbamoyl, di-[N-ethyl] aminosulphonyl or hydroxy.

14. A method of treatment of a bacterial infection in a human or other mammal in need thereof by administering an antibacterially effective amount of a carbapenem compound selected from the group consisting of (5R,6S,8R,2'S,4'S)-2-(2-(3,4-dihydroxyphenylcarbamoyl)pyrrolidin- 4-ylthio)-6-(1-hydroxyethyl)carbapenem-3-carboxylic acid;

(1R,5R,6S,8R,2'S,4'S)-2-(2-(5-cyano- 3,4-dihydroxyphenylcarbamoyl)pyrrolidin-4-ylthio)-6-(1-hydroxyethyl)-1-methylcarbapenem-3-carboxylic acid;

(5R,6S,8R,2'S,4'S)-2-(2-(5-bromo-3,4-dihydroxyphenylcarbamoyl)pyrrolidin- 4-ylthio)-6-(1-hydroxyethyl)carbapenem-3-carboxylic acid;

(1R,5R,6S,8R,2'S,4'S)-2-(2-( 3,4-dihydroxyphenylcarbamoyl)pyrrolidin-4-ylthio)-6-(1-hydroxyethyl)-1-methylcarbapenem-3-carboxylic acid;

(1R,5R,6S,8R,2'S,4'S)-2-(2-(5-methoxy- 3,4-dihydroxyphenylcarbamoyl)pyrrolidin-4-ylthio)-6-( 1-hydroxyethyl)-1-methylcarbapenem-3-carboxylic acid;

(1R,5R,6S,8R,2'S,4'S)-2-(2-(2,5-dichloro- 3,4-dihydroxyphenylcarbamoyl)pyrrolidin-4-ylthio)-6-( 1-hydroxyethyl)-1-methylcarbapenem-3-carboxylic acid;

(1R,5R,6S,8R,2'S,4'S)-2-(2-(5-hydroxy- 3,4-dihydroxyphenylcarbamoyl)pyrrolidin-4-ylthio)-6-( 1-hydroxyethyl)--methylcarbapenem-3-carboxylic acid;

(1R,5R,6S,8R,2'S,4'S)-2-(2-(5-bromo- 3,4-dihydroxyphenylcarbamoyl)pyrrolidin-4-ylthio)-6-( 1-hydroxyethyl)-1-methylcarbapenem-3-carboxylic acid;

(1R,5R,6S,8R,2'S,4'S)-2-(2-(5-N-methoxyiminomethyl-3,4-dihydroxyphenylcarbamoyl)pyrrolidin-4-ylthio)-6-( 1-hydroxyethyl)-1-methylcarbapenem-3-carboxylic acid;

(1R,5R,6S,8R,2'S,4'S)-2-(2-(6-methoxycarbonyl- 3,4-dihydroxyphenylcarbamoyl)pyrrolidin-4-ylthio)-6-( 1-hydroxyethyl)-1-methylcarbapenem-3-carboxylic acid;

(1R,5R,6S,8R,2'S,4'S)-2-(2-(6-carboxy- 3,4-dihydroxyphenylcarbamoyl)pyrrolidin-4-ylthio)-6-( 1-hydroxyethyl)-1-methylcarbapenem-3-carboxylic acid; and (1R,5R,6S,8R,2'S,4'S)-2-(2-(6-di-(N-ethyl)aminosulphonyl- 3,4-dihydroxyphenylcarbamoyl)pyrrolidin-4-ylthio)-6-( 1-hydroxyethyl)-1-methylcarbapenem-3-carboxylic acid;

or a pharmaceutically acceptable salt or in vivo hydrolysable ester thereof.

15. A compound of the formula (V)

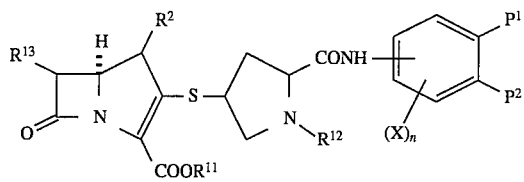

wherein $R^2$ is hydrogen or $C_{1-4}$alkyl;

$R^{11}$ is hydrogen or a carboxy protecting group;

$R^{12}$ is hydrogen or an amino protecting group;

$R^{13}$ 1-hydroxyethyl, 1-fluoroethyl, hydroxymethyl, or 1-(protected hydroxy)ethyl;

$P^1$ and $P^2$ are independently hydroxy or protected hydroxy; and $(X)_n$ represents up to three optional substituents which may be the same or different and are $C_{1-4}$alkyl, halo, hydroxy, hydroxy$C_{1-4}$alkyl, amino, nitro, $C_{1-4}$alkoxy, carboxy$C_{1-4}$alkyl, $C_{1-4}$alkanoylamino, N-alkyl-N-$C_{1-4}$alkanoylamino, trifluoromethyl, carboxy, carbamoyl, $C_{1-4}$alkylcarbamoyl, di-$C_{1-4}$alkylcarbamoyl, cyano, $C_{1-4}$alkoxycarbonyl, $C_{1-4}$alkylthio, $C_{1-4}$alkanesulphinyl, $C_{1-4}$alkanesulphonamido, $C_{1-4}$alkanoyl, $C_{1-4}$alkanoyloxy, $C_{1-4}$alkanesulphonyl, $C_{2-4}$alkenyl, hydroxyiminomethyl, $C_{1-4}$alkoxyiminomethyl, aminosulphonyl, N-$C_{1-4}$alkylaminosulphonyl or di-[N-$C_{1-4}$alkyl]aminosulphonyl.

* * * * *